United States Patent [19]
Schonauer et al.

[11] Patent Number: 5,969,232
[45] Date of Patent: Oct. 19, 1999

[54] CATALYTIC LAYER SYSTEM

[75] Inventors: Ulrich Schonauer, Eggenstein; Michael Tafferner, Malsch, both of Germany

[73] Assignee: Heraeus Electro-Nite International N.V., Belgium

[21] Appl. No.: 09/123,059

[22] Filed: Jul. 27, 1998

[30] Foreign Application Priority Data

Jul. 29, 1997 [DE] Germany .................... 197 32 601

[51] Int. Cl.$^6$ ............ G01N 27/00; B01J 21/06; H01C 7/00
[52] U.S. Cl. ............ 73/31.05; 73/23.2; 422/98; 204/192.25; 427/255.2
[58] Field of Search ............ 73/31.05, 23.2, 73/335.05; 422/83, 98; 204/192.25, 192.15; 427/255.2

[56] References Cited

U.S. PATENT DOCUMENTS

| | | | |
|---|---|---|---|
| 4,024,036 | 5/1977 | Nakamura et al. | 204/129 |
| 4,863,583 | 9/1989 | Kurachi et al. | 204/424 |
| 4,937,219 | 6/1990 | Haruta et al. | 502/174 |
| 4,977,658 | 12/1990 | Awano et al. | 29/25.01 |
| 5,018,380 | 5/1991 | Zupancio et al. | 73/23.2 |
| 5,086,286 | 2/1992 | Yasukawa et al. | 338/34 |
| 5,212,050 | 5/1993 | Mier et al. | 430/320 |
| 5,389,340 | 2/1995 | Satake | 422/98 |
| 5,578,283 | 11/1996 | Chen et al. | 423/240 R |
| 5,629,474 | 5/1997 | Williams | 73/23.2 |
| 5,698,267 | 12/1997 | Friese et al. | 427/430.1 |

FOREIGN PATENT DOCUMENTS

| | | |
|---|---|---|
| 0 360 159 B1 | 9/1989 | European Pat. Off. . |
| 38 13 930 C2 | 5/1992 | Germany . |
| 42 40 267 A1 | 6/1994 | Germany . |
| 43 39 737 C1 | 1/1995 | Germany . |
| 195 00 235 A1 | 7/1996 | Germany . |

*Primary Examiner*—Hezron Williams
*Assistant Examiner*—J. David Wiggins
*Attorney, Agent, or Firm*—Gerstman, Ellis & McMillin, Ltd.

[57] ABSTRACT

The invention relates to a catalytic layer system on a resistive gas sensor, especially on a resistive gas sensor layer on a titanate base, with at least one first layer and a second layer lying over the first layer, where, according to the invention, the first layer exhibits a catalytically active substance whose volume percentage in the layer ranges from 20 to 80%. In addition, the first layer contains a titanate that corresponds to at least one titanate of the underlying gas sensor layer. This attribute guarantees favorable adhesion between the layers. Furthermore, an oxide mixture that contributes to the improved mechanical stability of the layer system is provided in the second layer instead of the catalytically active substance. To manufacture the catalytic layer system, the individual layers are applied to the sensor in a screen printing process, which allows for a rational method of production and the precise dosing and distribution of the individual layer components.

10 Claims, No Drawings

CATALYTIC LAYER SYSTEM

BACKGROUND OF THE INVENTION

The invention relates to a catalytic layer system on a resistive gas sensor, especially on a resistive gas sensor layer based on a titanate, with at least one first layer and a second layer lying over the first layer, where at least one layer exhibits a catalytically active substance.

A gas sensor that is built up on a substrate using thick-film technology is known from EP 360 159 B1. Here, the gas-sensitive layer consisting of $SnO_2$, ZnO, $Fe_2O_3$, $TiO_2$ or CoO is soaked in a preferably aqueous solution of a platinum compound, such as chloro platinum acid. This is followed by a temperature treatment in the range of −5° C. to 180° C. in a reducing gas atmosphere and at a defined relative humidity. An additional temperature at more than 200° C. is necessary to optimize the desired precipitation of the precious metal in the gas-sensitive layer. Consequently, the entire impregnation process is very cumbersome and is characterized by a large number of individual steps which, based on their abundance alone, are prone to error in production terms. Furthermore, it should be noted that the impregnation process only improves the catalytic activity of the gas-sensitive layer itself in its interaction with the electrodes, but that this arrangement does not provide protection against mechanical influences or against compounds that act as catalyst poisons.

DE 42 40 267 A1 discloses an impregnation technology similar to the aforementioned state of the art. However, it is not used on a gas-sensitive layer, but rather in connection with the catalytic activation of a cermet electrode on an oxygen-ion-conducting solid electrolyte of a gas sensor. In this case, various platinum salt solutions are listed that are applied to a porous cermet electrode. To ensure better penetration into the pores of the electrode, 100 mbar to 1 bar of pressure is applied to the sensor element while it is being soaked in the platinum solution. Again, this is followed by a costly drying and baking procedure, partly in air and partly in a hydrogen stream. The sensor object disclosed in DE 42 40 267 is finger-shaped (a tube that is closed at one end), while the cermet electrodes are generally secured to the closed end of the finger-shaped object. Consequently, soaking of the cermet electrode is preferably achieved by dipping the electrodes, which are arranged on the spherical surface of the sensor body, into the fluid platinum solution. As this can easily lead to droplet formation, it is difficult to ensure a reproducible application quantity and, consequently, a uniform concentration of the catalytically active components penetrating into the electrode layer using this application technology. A porous, inert coating, which serves as a protective layer, is subsequently applied in one or more separate steps to this catalytically activated cermet electrode (e.g., by plasma spraying of a magnesium spinel).

Coating layers made of oxide mixtures of $SiO_2$, $Al_2O_3$ and BaO on electrical conductors and/or semiconductors are known from DE 195 00 235 A1. More or less porous layers are generated, depending on the BaO percentage and the baking temperature. A coating layer according to DE 195 00 235 for use on a gas-sensitive layer, e.g., of strontium titanate, only encompasses a protective function, as the catalytically active component is lacking. It also has the disadvantage that a mechanically tension-free bond with the underlying gas sensor layer cannot be achieved, as this oxide mixture does not contain the ceramic material of the gas-sensitive layer. Consequently, the $SiO_2$—$Al_2O_3$—BaO coating layer known from DE 195 00 235 lacks the attribute of catalytic action and a component that provides for favorable adhesion of the layer sequence to a sensitive layer.

DE 38 13 930 C2 describes a well-adhering electrode structure on an oxygen-ionconducting solid electrolyte made of $ZrO_2$ that is covered by a protective layer consisting of a ceramic material or by a ceramic "spacer layer". In a special embodiment, a catalyst layer that contains a platinum group metal is arranged over this first layer. This catalyst layer is, in turn, coated with a porous protective layer made of sprayed-on spinel (example 3). The entire layer structure consisting of a two-layer cermet electrode, a ceramic spacer layer, a catalyst layer and a ceramic coating layer is extremely complex and, due to the use of various application technologies (printing, plasma spraying), very costly in its manufacture.

Consequently, the objective of the invention is to provide a catalytically active layer system for a resistive gas sensor which, while possessing optimized diffusion properties (porosity), exhibits favorable adhesion to the underlying layer or interface by minimizing the differences in the thermal expansion behavior of the materials, and which exhibits favorable mechanical resistance to the possible effects of abrasive particles over long periods of time.

BRIEF SUMMARY OF THE INVENTION

In accordance with the present invention, in addition to the catalytically active substance, which comprises 20 to 80% in volume, the first layer contains a titanate that is identical to at least one titanate of the resistive gas sensor layer, and in which the second layer contains an oxide mixture of the oxides of Al, Si and Ba instead of the catalytically active substance in the first layer.

DETAILED DESCRIPTION OF ILLUSTRATIVE EMBODIMENTS

Sensors for monitoring and regulating exhaust gases from combustion systems are usually subjected to substantial stress resulting from high temperatures, temperature fluctuation, hot gas corrosion, vibrations, chemical compounds acting as catalyst poisons, etc. A catalytic layer system according to the invention is advantageous for purposes of maintaining the operativeness of such sensors. The minimum of two layers used in the structure of the catalytic layer system on the gas-sensitive layer ensures both favorable mechanical protection during the assembly of the sensor element in a casing, as well as against possible abrasive particles in the exhaust gas stream. The thickness of the individual layers generally ranges from 5 $\mu$m to 40 $\mu$m, so that a total layer package with a thickness of about 10 to 160 $\mu$m develops on the gas-sensitive layer. The layer system, particularly the first layer over the gas-sensitive layer, contains at least one catalytically active substance that comprises 20 to 80% in volume of this layer. The catalytic action is necessary to convert the gas percentage being measured in the gas stream into a component that is detectable for the sensitive layer. The remaining volume percentage of the first layer consists of a titanate that corresponds to at least one titanate in the underlying, resistive gas sensor layer. This feature provides for optimal adhesion between the gas-sensitive layer and the first catalytic layer, even if the gas-sensitive layer was already sintered at a high temperature.

As it is used in the invention, the term titanate refers to a double oxide according to the general formula $ABO_3$, where B is a quadrivalent titanium ion and A is one or more elements from the group Mg, Ca, Sr and Ba and/or compounds with the general formulas $M_4TiO_4$, $M_2TiO_3$, $M_2Ti_2O_5$, $M_2Ti_3O_7$ and $M_2Ti_9O_{20}$, which develop when titanium dioxide reacts with alkali hydroxides or alkali carbonates. According to the invention, the two titanates, which are largely identical in terms of their chemical composition, interact during the temperature treatment of the applied catalytic layer and enter into solid bonds at many small localized points. As this does not result in any relevant differences in the thermal expansion properties of the materials, inner mechanical stress in the bond is minimized during heating and cooling. In addition to the titanate, the first layer may also contain small amounts of a low-sintering substance that advantageously reduces the baking temperature for the first layer in the interest of preserving the catalytic effect.

The layer is characterized by a porosity of about 25 to 45% in volume. Thus, a favorable bond or adhesion is provided and the gas flow to be detected can be diffused in with adequate speed.

To lend greater mechanical stability to the entire layer system and ensure continued operativeness over longer periods of time, a second layer, which contains an oxide mixture of $SiO_2$, $Al_2O_3$ and BaO instead of the catalytically active substance in the first layer, is placed over the first layer. Because of this addition to the ceramic material of the first layer or the gas-sensitive layer, the porosity in the upper portion of the catalytic layer system is reduced. As a result, abrasive particles striking the surface of the sensor elements encounter increased resistance.

The use of a platinum group metal as the catalytically active substance is particularly advantageous. The term platinum group metal refers to elements in the group Pt, Pd, Rh, Ru, Os, Ir. The use of platinum or rhodium, or a mixture of these two metals, is preferable.

With respect to the catalytically active substance as a component in the layer system, it has proven to be advantageous if the substance in question, preferably a platinum group metal, is used in powder or flake form. The latter is also referred to as "flake". Preparations can also be used in which the platinum group metal is present in a form which is bonded to a resinate (such as Rhodium-Sulforesinate, made by W. C. Heraeus GmbH).

The use of strontium titanate as the titanate in the layer system is advantageous. Other titanates, such as calcium or barium titanate, or titanium oxide, can also be used.

It has proven to be advantageous if the oxide mixture in the second layer comprises 20 to 80% in volume of the second layer. Proportions of 40 to 60% in volume or 45 to 55% in volume are considered especially advantageous.

Production of the layer system by means of simple, rational production technology which, moreover, allows for improved dosage and local distribution of the catalytically active components, may, for example, be achieved in that the first and the second layer are applied in sequence by printing a paste onto the gas sensor layer and are subsequently sintered, with the paste for the first layer containing, in addition to a pasting agent, a catalytically active substance and a titanate that is identical to at least one titanate in the gas sensor layer, and with the paste for the second layer containing an oxide mixture of the oxides of Al, Si and Ba instead of the catalytic substance in the paste for the first layer.

Cellulose dissolved into organic solvents represents an example of the type of pasting agent that may be considered in this context. As a result of baking at about 850 to 1400° C., the organic components of the paste evaporate without residues and the layer is hardened by means of sintering. The ceramic material, a titanate which is present as a component of the gas sensor layer and of the catalytic layer system, provides for adhesion of the applied layer to the layer beneath it.

The screen printing process has proven to be effective in the manufacture of the catalytic layer system. The paste can be applied with considerable geometric precision in this process, thereby ensuring the correct dosage and distribution of all layer components.

In the following text, the invention is described in detail using examples of a catalytic layer system for a resistive lambda sensor on a strontium titanate base.

EXAMPLE 1

The following initial materials were selected to manufacture a paste, which is capable of being screen-printed, for the first layer of the catalytic layer system according to the invention:

Pt flakes, Degussa Company, product no. 64320001 $SrTiO_3$ powder Screen printing medium no. 80840, Cerdec Company, Frankfurt The powders and the screen printing medium are placed into an 80 ml agate beaker in proportions of 30 g platinum, 10 g $SrTiO_3$ powder and 16 g screen printing medium (also used as a pasting agent here) and, following the addition of 7 agate balls, are homogenized for 8 hours in a planetary ball mill.

To manufacture the paste for the second layer, 4.9 g $Al_2O_3$, 3.4 g $SiO_2$, 3.3 g BaO, 11.6 g $SrTiO_3$ and 12.5 g screen printing medium no. 80840 (Cerdec Company) are placed into an 80 ml agate beaker and, also following the addition of 7 agate balls, are homogenized for 8 hours in a planetary ball mill.

Using screen printing, pastes 1 and 2 are applied in sequence to an $SrTiO_3$ sensor layer of a lambda sensor. After each screen printing step, the products are dried for 10 minutes at 120° C. The subsequent baking process is based on the following sintering profile:

1. Heat to 350° C. at a heating rate of 10 K/minute;
2. 30 minutes hold time at 350° C.;
3. Heat to 1330° C. at a heating rate of 10 K/minute;
4. 60 minutes hold time at 1330° C.;
5. Cool to room temperature at a cooling rate of 10 K/minute.

EXAMPLE 2

To manufacture the paste for the first layer of the catalytic layer system according to the invention, 11.6 g $SrTiO_3$, 4.9 g $Al_2O_3$, 3.4 g $SiO_2$, 3.3 g BaO and a solution of 0.5 g rhodium sulforesinate in 5 ml terpineol are placed into an agate beaker with 20 g n-hexane and, following the addition of 7 agate balls, are homogenized for 0.5 hours. The n-hexane is then volatilized. Subsequently, a pasting agent consisting of 10 g screen printing medium no. 80840 (Cerdec Company) is added and the mixture is again homogenized for 4 hours in a planetary ball mill.

The paste for the second layer is manufactured as described in example 1. Both the screen printing onto an $SrTiO_3$ sensor layer of a lambda sensor and the sintering of pastes 1 and 2 from example 2 are performed essentially as described in example 1. In this case, however, the product is only heated to 1250° C. and the hold time at 1250° C. is only 30 minutes instead of 60 minutes.

Using the materials and procedures described in examples 1 and 2, a catalytic layer system which, according to example 1, contains platinum as a catalytically active substance amounting to about 50% in volume of the first layer, is generated on a resistive gas sensor layer.

In example 2, however, rhodium is used as the catalytically active substance. In addition to the ceramic material of the sensitive layer, i.e., $SrTiO_3$, the first layer also contains the oxide mixture of the second layer, i.e., an oxide mixture of $Al_2O_3$, $SiO_2$ and BaO.

What is claimed:

1. A catalytic layer system for an electrically resistive gas sensor comprising:

a first layer on top of a resistive gas sensor layer deposited on a substrate, and comprising 20 to 80% by volume of a catalytically active substance and a titanate;

a second layer lying over the first layer comprising the same titanate as used in the first layer and an oxide mixture of oxides of Al, Si and Ba used instead of the cataytically active substance of the first layer.

2. The catalytic layer system of claim 1 wherein the first layer comprises 40–60% by volume of a catalytically active substance.

3. The catalytic layer system of claim 1 wherein the first layer comprises 45–55% by volume of a catalytically active substance.

4. The catalytic layer system of claim 1 wherein the catalytically active substance comprises a platinum group metal.

5. The catalytic layer system of claim 1 wherein the catalytically active substance comprises platinum or rhodium.

6. The catalytic layer system of claim 4 wherein the platinum group metal is introduced into the layer system in powder or flake form.

7. The catalytic layer system of claim 1 wherein the titanate consists essentially of strontium titanate.

8. The catalytic layer system of claim 1 wherein the oxide mixture comprises 20–80% by volume of the second layer.

9. The catalytic layer system of claim 1 wherein the oxide mixture comprises 40–60% by volume of the second layer.

10. The catalytic layer system of claim 1 wherein the oxide mixture comprises 45–55% by volume of the second layer.

* * * * *